(12) United States Patent
Whittingham et al.

(10) Patent No.: US 9,044,014 B2
(45) Date of Patent: Jun. 2, 2015

(54) HERBICIDAL COMPOSITIONS

(75) Inventors: William Guy Whittingham, Berkshire (GB); Mark Spinney, Berkshire (GB); Gavin John Hall, Berkshire (GB); Natalie Dupen, Berkshire (GB)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 14/123,445

(22) PCT Filed: May 31, 2012

(86) PCT No.: PCT/EP2012/060236
§ 371 (c)(1),
(2), (4) Date: Dec. 2, 2013

(87) PCT Pub. No.: WO2012/164013
PCT Pub. Date: Dec. 6, 2012

(65) Prior Publication Data
US 2014/0121106 A1    May 1, 2014

(30) Foreign Application Priority Data
Jun. 2, 2011 (EP) .................................... 1109309

(51) Int. Cl.
*A01N 25/32* (2006.01)
*A01N 43/40* (2006.01)

(52) U.S. Cl.
CPC ...................................... *A01N 43/40* (2013.01)

(58) Field of Classification Search
None
See application file for complete search history.

(56) References Cited

U.S. PATENT DOCUMENTS

2007/0179060 A1 *  8/2007  Balko et al. ................... 504/193

FOREIGN PATENT DOCUMENTS

| EP | 365484 | * | 4/1990 |
| EP | 2191719 | * | 6/2010 |

OTHER PUBLICATIONS

International Search Report, International Application No. PCT/EP2012/060236, completion date: Aug. 21, 2012.

* cited by examiner

*Primary Examiner* — Alton Pryor
(74) *Attorney, Agent, or Firm* — James Cueva

(57) ABSTRACT

The present invention relates to compositions for protecting crop of useful plants from the harmful effects of certain pyridine derivative herbicides as well as methods for protecting crops of useful plants from the harmful effects of these herbicides and methods for combating weeds in crops of useful plants.

13 Claims, No Drawings

HERBICIDAL COMPOSITIONS

This application is a 371 of International Application No. PCT/EP2012/060236 filed May 31, 2012, which claims priority to EP 1109309.3, filed Jun. 2, 2011, the contents of which are incorporated herein by reference.

The present invention relates to compositions comprising certain herbicidal pyridine derivatives and a safener and methods for protecting cultivated plants from the damaging effects of the herbicidal pyridine derivatives.

It is known that when herbicides are used to control the growth of undesired plants, there may be some damage to the cultivated plants. The amount of damage will depend on a number of factors but, in some cases, the cultivated plants can be protected from the effect of the herbicide by using a compound termed a safener.

Surprisingly, it has now been found that certain herbicidal pyridine derivatives can be safened by N-(2-methoxybenzoyl)-4-[methylaminocarbonyl)amino]benzenesulfonamide.

Accordingly, the present invention provides a composition for protecting crop plants from the harmful effects of a pyridine derivative herbicide of formula (I)

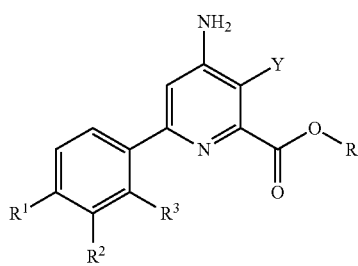

or a salt or N-oxide thereof wherein

Y is chloro or bromo,

R is hydrogen, $C_{1-8}$ alkyl, $C_{2-5}$ alkenyl, $C_{3-5}$ alkynyl, aryl $C_{1-2}$ alkyl-, $C_{1-4}$ alkoxy $C_{1-4}$ alkyl- or $C_{1-4}$ alkoxy $C_{1-4}$ alkoxy $C_{1-2}$ alkyl-, $R^1$ is chloro or bromo, $R^2$ is $C_{1-2}$ alkoxy, $R^3$ is chloro or fluoro.

and wherein said composition comprises, in addition to the pyridine derivative herbicide of formula (I), the safener N-(2-methoxybenzoyl)-4-[(methylaminocarbonyl)amino]benzenesulfonamide.

"Alkyl" means a linear saturated monovalent hydrocarbon radical of one to eight carbon atoms or a branched saturated monovalent hydrocarbon radical of three to eight carbon atoms, e.g. methyl, ethyl, n-propyl, iso-propyl, n-butyl, sec-butyl, iso-butyl, tert-butyl, and the like. Suitably, linear alkyl groups contain one to eight, one to six, one to five or one to four carbon atoms, more suitably are selected from methyl, ethyl or n-propyl and, most suitably, are methyl or ethyl. Suitably, branched alkyl groups contain three to eight, three to six or three to five carbon atoms and more suitably are selected from iso-propyl, sec-butyl, iso-butyl or tert-butyl. It is noted that this definition applies both when the term is used alone and when it is used as part of a compound term, such as "haloalkyl" and similar terms.

"Alkenyl" means a linear monovalent unsaturated hydrocarbon radical of two to five carbon atoms, or a branched monovalent hydrocarbon radical of three to five carbon atoms containing at least one double bond, e.g. ethenyl, propenyl and the like. Where appropriate, an alkenyl group can be of either the (E)- or (Z)-configuration. Suitably, linear alkenyl groups contain two to five carbon atoms, more suitably two to four carbon atoms and, most suitably are ethenyl (vinyl), prop-1-enyl (1-propenyl) or prop-2-enyl (allyl). Suitably, branched alkenyl groups contain three to five carbon atoms, more suitably from three to four and, most suitably, are 1-methylethenyl (2-propenyl), 1-methylprop-1-enyl, 1-methylprop-2-enyl, 2-methylprop-1-enyl and 2-methylprop-2-enyl (2-methylallyl).

"Alkynyl" means a linear monovalent unsaturated hydrocarbon radical of three to five carbon atoms, or a branched monovalent hydrocarbon radical of four to five carbon atoms, containing at least one triple bond e.g. propynyl and the like. Suitably, alkynyl groups contain three to five carbon atoms and more suitably three to four carbon atoms e.g. prop-1-ynyl, prop-2-ynyl, but-1-ynyl, but-2-ynyl and but-3-ynyl.

"Alkoxy" means a radical —OR, where R is alkyl as defined above. Alkoxy groups include, but are not limited to, methoxy, ethoxy, 1-methylethoxy, propoxy, butoxy, 1-methylpropoxy and 2-methylpropoxy. Preferably alkoxy means methoxy or ethoxy.

"Alkoxyalkyl" means a radical —ROR, where each R is, independently, alkyl as defined above.

"Alkoxyalkoxyalkyl" means a radical —ROROR, wherein each R is, independently, alkyl as defined above.

"Aryl" or "aromatic ring" refers to an aromatic substituent which may be a single ring or multiple rings which are fused together, linked covalently or linked to a common group such as an ethylene (—$CH_2$—$CH_2$—) or methylene (—$CH_2$—) moiety. Representative examples of aryl include, for example, phenyl, naphthyl, azulenyl, indanyl, indenyl, anthracenyl, phenanthrenyl, tetrahydronaphthyl, biphenyl, diphenylmethyl and 2,2-diphenyl-1-ethyl. Preferred aryl groups are phenyl and naphthyl groups.

"Halo" or "halogen" means fluoro, chloro, bromo or iodo, preferably chloro or fluoro.

"Arylalkyl" means —R-aryl, wherein R is an alkyl group as defined above.

The compounds of formula I may exist in different geometric or optical isomeric forms or in different tautomeric forms. One or more centres of chirality may be present, in which case compounds of the formula I may be present as pure enantiomers, mixtures of enantiomers, pure diastereomers or mixtures of diastereomers. There may be double bonds present in the molecule, such as C=C or C=N bonds, in which case compounds of formula I may exist as single isomers or mixtures of isomers. Centres of tautomerisation may be present. This invention covers all such isomers and tautomers and mixtures thereof in all proportions as well as isotopic forms such as deuterated compounds.

Suitable salts include those formed by contact with acids or bases. Suitable salts of the compounds of formula I thus include those derived from alkali or alkaline earth metals and those derived from ammonia and amines. Preferred cations include sodium, potassium, magnesium, and ammonium cations of the formula $N^+(R^iR^jR^kR^l)$ wherein $R^i$, $R^j$, $R^k$ and $R^l$ are independently selected from hydrogen, $C_{1-6}$ alkyl and $C_{1-6}$ hydroxyalkyl. Salts of the compounds of formula I can be prepared by treatment of compounds of formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable salts of the compounds of formula I also include acid addition salts such as those with an inorganic acid such as hydrochloric, hydrobromic, sulphuric, nitric or phosphoric acid, an organic acid such as acetic, butyric, propionic or hexanoic, an organic carboxylic acid such as citric, fumaric, lactic, maleic, malonic, mandelic, malic, oxalic, succinic, tartaric, toluic or phthalic acid, or a sulphonic acid such as methane, benzene, naphthalene, camphor or toluene sulphonic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In particularly preferred embodiments of the invention, the preferred groups for Y, R, $R^1$, $R^2$ and $R^3$, in any combination thereof, are as set out below.

In a preferred embodiment, Y is chloro.

In a preferred embodiment, R is hydrogen, $C_{1-4}$ alkyl, $C_{3-4}$ alkenyl, arylmethyl, $C_{1-4}$ alkoxy $C_{1-2}$ alkyl. In a more preferred embodiment, R is hydrogen or methyl. In a particular embodiment, when R is hydrogen, there is provided a salt of the compound of formula (I) as described or listed above. In particular, the salt of the compound of formula (I) may be derived from an alkali metal, an alkaline earth metal, ammonia or an amine. Preferably, the salt is a sodium salt, a potassium salt or a triethylammonium salt.

In a preferred embodiment, $R^1$ is chloro.
In a preferred embodiment, $R^2$ is methoxy.
In a preferred embodiment, $R^3$ is fluoro.

The compounds described below are illustrative of compounds of Formula (I) featured in the composition of the invention. Table 1 below provides 50 compounds designated compounds 1-1 to 1-50 respectively, of formula (I).

| Compound Number | Y | $R^1$ | $R^2$ | $R^3$ | R |
|---|---|---|---|---|---|
| 1 | Cl | Cl | $OCH_3$ | Cl | H |
| 2 | Cl | Br | $OCH_3$ | Cl | H |
| 3 | Cl | Cl | $OCH_2CH_3$ | Cl | H |
| 4 | Cl | Br | $OCH_2CH_3$ | Cl | H |
| 5 | Cl | Cl | $OCH_3$ | F | H |
| 6 | Cl | Br | $OCH_3$ | F | H |
| 7 | Cl | Cl | $OCH_2CH_3$ | F | H |
| 8 | Cl | Br | $OCH_2CH_3$ | F | H |
| 9 | Br | Cl | $OCH_3$ | Cl | H |
| 10 | Br | Br | $OCH_3$ | Cl | H |
| 11 | Br | Cl | $OCH_2CH_3$ | Cl | H |
| 12 | Br | Br | $OCH_2CH_3$ | Cl | H |
| 13 | Br | Cl | $OCH_3$ | F | H |
| 14 | Br | Br | $OCH_3$ | F | H |
| 15 | Br | Cl | $OCH_2CH_3$ | F | H |
| 16 | Br | Br | $OCH_2CH_3$ | F | H |
| 17 | Cl | Cl | $OCH_3$ | Cl | $CH_3$ |
| 18 | Cl | Br | $OCH_3$ | Cl | $CH_3$ |
| 19 | Cl | Cl | $OCH_2CH_3$ | Cl | $CH_3$ |
| 20 | Cl | Br | $OCH_2CH_3$ | Cl | $CH_3$ |
| 21 | Cl | Cl | $OCH_3$ | F | $CH_3$ |
| 22 | Cl | Br | $OCH_3$ | F | $CH_3$ |
| 23 | Cl | Cl | $OCH_2CH_3$ | F | $CH_3$ |
| 24 | Cl | Br | $OCH_2CH_3$ | F | $CH_3$ |
| 25 | Br | Cl | $OCH_3$ | Cl | $CH_3$ |
| 26 | Br | Br | $OCH_3$ | Cl | $CH_3$ |
| 27 | Br | Cl | $OCH_2CH_3$ | Cl | $CH_3$ |
| 28 | Br | Br | $OCH_2CH_3$ | Cl | $CH_3$ |
| 29 | Br | Cl | $OCH_3$ | F | $CH_3$ |
| 30 | Br | Br | $OCH_3$ | F | $CH_3$ |
| 31 | Br | Cl | $OCH_2CH_3$ | F | $CH_3$ |
| 32 | Br | Br | $OCH_2CH_3$ | F | $CH_3$ |
| 33 | Cl | Cl | $OCH_3$ | Cl | $CH_2CH_3$ |
| 34 | Cl | Cl | $OCH_3$ | F | $CH_2CH_3$ |
| 35 | Cl | Cl | $OCH_3$ | Cl | $CH_2CH_2CH_3$ |
| 36 | Cl | Cl | $OCH_3$ | F | $CH_2CH_2CH_3$ |
| 37 | Cl | Cl | $OCH_3$ | Cl | $CH_2CH_2CH_2CH_3$ |
| 38 | Cl | Cl | $OCH_3$ | F | $CH_2CH_2CH_2CH_3$ |
| 39 | Cl | Cl | $OCH_3$ | Cl | $CH_2CH=CH_2$ |
| 40 | Cl | Cl | $OCH_3$ | F | $CH_2CH=CH_2$ |
| 41 | Cl | Cl | $OCH_3$ | Cl | $CH_2C\equiv CH$ |
| 42 | Cl | Cl | $OCH_3$ | F | $CH_2C\equiv CH$ |
| 43 | Cl | Cl | $OCH_3$ | Cl | $CH_2CH_2OCH_2CH_2CH_3$ |
| 44 | Cl | Cl | $OCH_3$ | F | $CH_2CH_2OCH_2CH_2CH_3$ |
| 45 | Cl | Cl | $OCH_3$ | Cl | Na salt |
| 46 | Cl | Cl | $OCH_3$ | F | Na salt |
| 47 | Cl | Cl | $OCH_3$ | Cl | K salt |
| 48 | Cl | Cl | $OCH_3$ | F | K salt |
| 49 | Cl | Cl | $OCH_3$ | Cl | $Et_3N$ salt |
| 50 | Cl | Cl | $OCH_3$ | F | $Et_3N$ salt |

These pyridine compounds used in the safened compositions of the present invention may be made as the skilled man will appreciate by applying and/or adapting as appropriate, the methods described in the prior art (see for example WO 2007/082098 and US2010/0311981).

The safener of the invention is disclosed in EP 0 365 484 A and may be made using the methods described therein.

Preferably the mixing ratio of compound of formula (I) to safener is from 100:1 to 1:100, especially from 20:1 to 1:20.

In a further aspect, the present invention provides a method for protecting crops of useful plants from the harmful effects of a herbicide of formula (I) as defined herein, which comprises applying to the locus of the useful plants the safener N-(2-methoxybenzoyl)-4-[methylaminocarbonyl)amino]benzenesulfonamide.

In a still further aspect, the present invention provides a method for combating weeds in crops of useful plants, which comprises treating the useful plants, seeds or cuttings thereof or the locus of the useful plants simultaneously or at separate times with a herbicidally active amount of a compound of formula (I) and the safener N-(2-methoxybenzoyl)-4-[methylaminocarbonyl)amino]benzenesulfonamide.

Any method of application to weeds/crop of useful plant, or locus thereof, which is routinely used in agriculture may be used, for example application by spray or broadcast method typically after suitable dilution of the composition of the invention.

The term "locus" as used herein includes not only areas where weeds may already be growing, but also areas where weeds have yet to emerge, and also to areas under cultivation with respect to crops of useful plants. Areas under cultivation include land on which the crop plants are already growing and land intended for cultivation with such crop plants.

Crops of useful plants in which compositions of the invention may be used or the methods of the invention applied include perennial crops, such as citrus fruit, grapevines, nuts, oil palms, olives, pome fruit, stone fruit and rubber, and annual arable crops, such as cereals, for example barley and wheat, cotton, oilseed rape, maize (including sweet corn), rice, sorghum, soy beans, sugar beet, sugar cane, sunflowers, ornamentals and vegetables, especially cereals and maize. In particular, the compositions of the invention may be used on maize (including sweet corn), sorghum, sugar cane and rice, more particularly, on maize, sugar cane and rice and most particularly on maize.

Compositions and methods of the invention may also be used on turf, pasture, rangeland, rights of way etc. In particular they may be used on golf-courses, lawns, parks, sportsfields, race-courses and the like.

Crops are to be understood as also including those crops which have been rendered tolerant to herbicides or classes of herbicides (e.g. ALS-, ACCase-, GS-, EPSPS-, PPO- and HPPD-inhibitors and synthetic auxins) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

The term "weeds" as used herein means any undesired plant, and thus includes not only agronomically important weeds as described below, but also volunteer crop plants.

Compounds of formula (I) may be used against a large number of agronomically important weeds. The weeds that may be controlled include both monocotyledonous and dicotyledonous weeds, such as, for example, *Alisma* spp, *Leptochloa chinensis, Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus* and especially *Cyperus iria, Abutilon, Sida, Xanthium, Amaranthus, Chenopodium, Ipomoea, Chrysanthemum, Galium, Viola, Veronica, Bidens, Euphorbia, Ischaemum, Polygonum, Helianthus, Panicum, Eriochloa, Brachiaria, Cenchrus, Commelina, Spermacoce, Senna, Tridax, Richardia, Chamaesyce*, and *Conyza* spp.

The compositions according to the invention are suitable for all the conventional methods of application in agriculture, such as, e.g., pre-emergent application, post-emergent application and seed dressing. Depending on the intended use, the safener can be employed for pre-treatment of the seed of the crop plant (dressing of the seed or cuttings) or can be introduced into the soil before or after sowing. However, it can also be applied by itself or together with the herbicide before or after emergence of the plants. The treatment of the plants or seed with the safener can therefore in principle be carried out independently of the time of application of the herbicide. Treatment of the plants by simultaneous application of the herbicide and safener (e.g., as a tank mix) is as a rule preferred. The application rate of safener to herbicide to be applied largely depends of the method of use. For field treatment, as a rule 0.001 to 5.0 kg of safener/ha, preferably 0.01 to 0.5 kg safener/ha and as a rule between 0.005 to 2 kg of herbicide/ha, but preferably between 0.001 to 1 kg/ha are applied. For seed dressing, in general 0.001 to 10 g of safener/kg seed, preferably 0.05 to 2 g safener/kg seed are applied. If the safener is applied in liquid form, with soaking of the seed, shortly before sowing, safener solutions which contain the safener in a concentration of 1 to 10,000, preferably 100 to 1000 ppm are expediently used.

The safened compositions of the present invention can be employed in unchanged form as a herbicidal composition. However, as a rule the compositions of the invention are preferably formulated in various ways using formulation adjuvants, such as carriers, solvents and surface-active substances, for example, as described hereinafter. Accordingly, the present invention provides a composition of the invention which further comprises at least one agriculturally acceptable adjuvant or diluent.

The formulated compositions can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, suspension concentrates, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. The formulated compositions can be in the form of concentrates which are diluted prior to use, although ready-to-use formulations can also be made. The dilutions can be made, for example, with water, liquid fertilisers, micronutrients, biological organisms, oil or solvents.

The formulated compositions can be prepared e.g. by mixing the active ingredient and safener combination with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules usually have a diameter of from 0.1 to 500 microns. Typically, they will contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other known polymers. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid (e.g. butyl acetate, ethyl acetate, isoamyl acetate, amyl acetate), diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, methanol, ethanol, isopropanol, and alcohols of higher molecular weight, such as amyl alcohol, tetrahydrofurfuryl alcohol, hexanol, octanol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances may advantageously be used in the formulations, especially in those formulations designed to be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride; polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in such formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers. An example of such an adjuvant is ammonium sulphate.

The formulated compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_{8-22}$ fatty acids, especially the methyl derivatives of $C_{12-18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Another preferred adjuvant is Adigor® (Syngenta AG) which is a methylated rapeseed oil-based adjuvant.

The application and action of the oil additives can be further improved by combination with surface-active substances, such as non-ionic, anionic or cationic surfactants. Examples of suitable anionic, non-ionic and cationic surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12-22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

Formulated compositions of the invention generally comprise from 0.1 to 99% by weight, especially from 0.1 to 95% by weight, of active compound mixture of the compound of formula (I) with a safener and from 1 to 99.9% by weight of a formulation adjuvant which preferably includes from 0 to 25% by weight of a surface-active substance. Whereas commercial products will preferably be formulated as concentrates, the end user will normally employ dilute formulations.

Various methods and techniques are suitable for using safeners or compositions containing them for protecting crop plants from the harmful actions of herbicides of formula I, such as, for example, the following:

i) Seed Dressing
  a) Dressing of the seed with the safener formulated as a wettable powder by shaking in a vessel until uniform distribution over the seed surface is achieved (dry dressing). About 1 to 500 g of safener (4 g to 2 kg of wettable powder) per 100 kg of seed are used here.
  b) Dressing of the seed with an emulsion concentrate of the safener by method a) (wet dressing).
  c) Dressing by immersing the seed in a liquor with 100-1000 ppm of safener for 1 to 72 hours and optionally subsequent drying of the seed (immersion dressing).

The dressing of the seed or the treatment of the sprouted seed are preferred methods of application, because the treatment with the safener is directed entirely at the target crop. As a rule, 1 to 1000 g of safener, preferably 5 to 250 g of safener are used per 100 kg of seed, it being possible to deviate upwards or downwards from the limit concentrations stated (repeat dressing), depending on the methods, which also allows the addition of other active compounds or micronutrients.

ii) Application as a Tank Mix
A liquid processed mixture of safener and herbicide of formula I (reciprocal ratio of amounts between 10:1 and 1:100) is used, the application rate of herbicide being 0.005 to 5.0 kg per hectare, alternatively from 0.001 to 1.0 kg per hectare. Such tank mixes are applied before or after sowing.

iii) Application into the Seed Furrow
The safener is introduced into the open sown seed furrow as an emulsion concentrate, wettable powder or as granules. After the seed furrow has been covered, the herbicide is applied by the pre-emergent method in a conventional method.

iv) Controlled Release of the Safener
The safener is absorbed in solution on to mineral carrier granules or polymerised granules (urea/formaldehyde) and dried. A coating which allows the safener to be released over a certain period of time can optionally be applied (coated granules).

In particular, preferred formulations have the following composition (%=percent by weight; active mixture of active compounds means the mixture of a compound of formula I with a safener):

Emulsifiable Concentrates

Active mixture of active compounds: 1 to 95%, preferably 60 to 90%
Surface-active agent: 1 to 30%, preferably 5 to 20%
Liquid carrier: 1 to 80%, preferably 1 to 35%

Dusts

Active mixture of active compounds: 0.1 to 10%, preferably 0.1 to 5%
Solid carrier: 99.9% to 90%, preferably 99.9 to 99%

Suspension Concentrates

Active mixture of active compounds: 5 to 75%, preferably 10 to 50%
Water: 94 to 24%, preferably 88 to 30%
Surface-active agent: 1 to 40%, preferably 2 to 30%

Wettable Powders

Active mixture of active compounds: 0.5 to 90%, preferably 1 to 80%
Surface-active agent: 0.5 to 20%, preferably 10 to 15%
Solid carrier: 5 to 95%, preferably 15 to 90%

Granules

Active mixture of active compounds: 0.1 to 30%, preferably 0.1 to 15%
Solid carrier: 99.5 to 70%, preferably 97 to 85%
Formulation examples for mixtures of herbicides of formula (I) with safeners (%=% by weight; EO=ethylene oxide)

| F1. Emulsifiable concentrates | a) | b) | c) | d) |
|---|---|---|---|---|
| active compound mixture | 5% | 10% | 25% | 50% |
| calcium dodecylbenzenesulfonate | 6% | 8% | 6% | 8% |
| castor oil polyglycol ether (36 mol of EO) | 4% | — | 4% | 4% |
| octylphenol polyglycol ether (7-8 mol of EO) | — | 4% | — | 2% |
| N-methyl pyrrolidone | — | — | 10% | 20% |
| arom. hydrocarbon mixture ($C_9$-$C_{12}$) | 85% | 78% | 55% | 16% |

Emulsions of any desired concentration can be obtained from such concentrates by dilution with water.

| F2. Solutions | a) | b) | c) | d) |
|---|---|---|---|---|
| active compound mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture ($C_9$-$C_{12}$) | 75% | 60% | — | — |

The solutions are suitable for use in the form of microdrops.

| F3. Wettable powders | a) | b) | c) | d) |
|---|---|---|---|---|
| active compound mixture | 5% | 25% | 50% | 80% |
| sodium lignosulfonate | 4% | — | 3% | — |
| sodium lauryl sulphate | 2% | 3% | — | 4% |
| sodium diisobutylnaphthalene-sulfonate | — | 6% | 5% | 6% |
| octylphenol polyglycol ether (7-8 mol EO) | — | 1% | 2% | — |
| highly dispersed silicic acid | 1% | 3% | 5% | 10% |
| kaolin | 88% | 62% | 35% | — |

The active compound mixture is mixed thoroughly with the adjuvants and the resulting mixture is thoroughly ground in a suitable mill, affording wettable powders which can be diluted with water to give suspensions of any desired concentration.

| F4. Coated granules | a) | b) | c) |
|---|---|---|---|
| active compound mixture | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active compound mixture is dissolved in methylene chloride and applied to the carrier by spraying, and the solvent is then evaporated off in vacuo.

| F5. Coated granules | a) | b) | c) |
|---|---|---|---|
| active compound mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active compound mixture is uniformly applied, in a mixer, to the carrier moistened with polyethylene glycol. Non-dusty coated granules are obtained in this manner.

| F6. Extruded granules | a) | b) | c) | d) |
|---|---|---|---|---|
| active compound mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active compound mixture is mixed and ground with the adjuvants, and the mixture is moistened with water. The mixture is extruded and then dried in a stream of air.

| F7. Dusts | a) | b) | c) |
|---|---|---|---|
| active compound mixture | 0.1% | 1% | 5% |
| talcum | 39.9% | 49% | 35% |
| kaolin | 60.0% | 50% | 60% |

Ready-to-use dusts are obtained by mixing the active compound mixture with the carriers and grinding the mixture in a suitable mill.

| F8. Suspension concentrates | a) | b) | c) | d) |
|---|---|---|---|---|
| active compound mixture | 3% | 10% | 25% | 50% |
| ethylene glycol | 5% | 5% | 5% | 5% |
| nonylphenol polyglycol ether (15 mol EO) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active compound mixture is intimately mixed with the adjuvants, giving a suspension concentrate from which suspensions of any desired concentration can be obtained by dilution with water.

It is often more practical to formulate the active compound of formula I and the safener individually and then to bring them together as a 'tank mix' in water in the application in the desired mixing ratio shortly before application.

The compositions of the present invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I) and the safener.

Where a composition of the invention is combined with at least one additional herbicide, the following mixtures of the composition of the invention are particularly preferred: composition of the invention+acetochlor, composition of the invention+acifluorfen, composition of the invention+acifluorfen-sodium, composition of the invention+aclonifen, composition of the invention+acrolein, composition of the invention+alachlor, composition of the invention+alloxydim, composition of the invention+allyl alcohol, composition of the invention+ametryn, composition of the invention+amicarbazone, composition of the invention+amidosulfuron, composition of the invention+aminocyclopyrachlor, composition of the invention+aminopyralid, composition of the invention+amitrole, composition of the invention+ammonium sulfamate, composition of the invention+anilofos, composition of the invention+asulam, composition of the invention+atrazine, composition of the invention+aviglycine, composition of the invention+azafenidin, composition of the invention+azimsulfuron, composition of the invention+BCPC, composition of the invention+beflubutamid, composition of the invention+benazolin, composition of the invention+bencarbazone, composition of the invention+benfluralin, composition of the invention+benfuresate, composition of the invention+bensulfuron, composition of the invention+bensulfuron-methyl, composition of the invention+bensulide, composition of the invention+bentazone, composition of the invention+benzfendizone, composition of the invention+benzobicyclon, composition of the invention+benzofenap, composition of the invention+bifenox, composition of the invention+bilanafos, composition of the invention+bispyribac, composition of the invention+bispyribac-sodium, composition of the invention+borax, composition of the invention+bromacil, composition of the invention+bromobutide, composition of the invention+bromophenoxim, composition of the invention+bromoxynil, composition of the invention+butachlor, composition of the invention+butafenacil, composition of the invention+butamifos, composition of the invention+butralin, composition of the invention+butroxydim, composition of the invention+butylate, composition of the invention+cacodylic acid, composition of the invention+calcium chlorate, composition of the invention+cafenstrole, composition of the invention+carbetamide, composition of the invention+carfentrazone, composition of the invention+carfentrazone-ethyl, composition of the invention+CDEA, composition of the invention+CEPC, composition of the invention+chlorflurenol, composition of the invention+chlorflurenol-methyl, composition of the invention+chloridazon, composition of the invention+chlorimuron, composition of the invention+chlorimuron-ethyl, composition of the invention+chloroacetic acid, composition of the invention+chlorotoluron, composition of the invention+chlorpropham, composition of the invention+chlorsulfuron, composition of the invention+chlorthal, composition of the invention+chlorthal-dimethyl, composition of the invention+cinidon-ethyl, composition of the invention+cinmethylin, composition of the invention+cinosulfuron, composition of the invention+cisanilide, composition of the invention+clethodim, composition of the invention+clodinafop, composition of the invention+clodinafop-propargyl, composition of the invention+clomazone, composition of the invention+clomeprop, composition of the invention+clopyralid, composition of the invention+cloransulam, composition of the invention+cloransulam-methyl, composition of the invention+CMA, composition of the invention+4-CPB, composition of the invention+CPMF, composition of the invention+4-CPP, composition of the invention+CPPC, composition of the invention+cresol, composition of the invention+cumyluron, composition of the invention+cyanamide, composition of the invention+cyanazine, composition of the invention+cycloate, composition of the invention+cyclosulfamuron, composition of the invention+cycloxydim, composition of the invention+cyhalofop, composition of the invention+cyhalofop-butyl, composition of the invention+2,4-D, composition of the invention+3,4-DA, composition of the invention+daimuron, composition of the invention+dalapon, composition of the invention+dazomet, composition of the invention+2,4-DB, composition of the invention+3,4-DB, composition of the invention+2,4-DEB, composition of the invention+desmedipham, composition of the invention+desmetryn, composition of the invention+dicamba, composition of the invention+dichlobenil, composition of the invention+ortho-dichlorobenzene, composition of the invention+para-dichlorobenzene, composition of the invention+dichlorprop, composition of the invention+dichlorprop-P, composition of the invention+diclofop, composition of the invention+diclofop-methyl, composition of the invention+diclosulam, composition of the invention+difenzoquat, composition of the invention+difenzoquat metilsulfate, composition of the invention+diflufenican, composition of the invention+diflufenzopyr, composition of the invention+dimefuron, composition of the invention+dimepiperate, composition of the invention+dimethachlor, composition of the invention+dimethametryn, composition of the invention+dimethenamid, composition of the invention+dimethenamid-P, composition of the invention+dimethipin, composition of the invention+dimethylarsinic acid, composition of the invention+dinitramine, composition of the invention+dinoterb, composition of the invention+diphenamid, composition of the invention+dipropetryn, composition of the invention+diquat, composition of the invention+diquat dibromide, composition of the invention+dithiopyr, composition of the invention+diuron, composition of the invention+DNOC, composition of the invention+3,4-DP, composition of the invention+DSMA, composition of the invention+EBEP, composition of the invention+endothal, composition of the invention+EPTC, composition of the invention+esprocarb, composition of the invention+ethalfluralin, composition of the invention+ethametsulfuron, composition of the invention+ethametsulfuron-methyl, composition of the invention+ethephon, composition of the invention+ethofumesate, composition of the invention+ethoxyfen, composition of the invention+ethoxysulfuron, composition of the invention+etobenzanid, composition of the invention+fenoxaprop, composition of the invention+fenoxaprop-P, composition of the invention+fenoxaprop-ethyl, composition of the invention+fenoxaprop-P-ethyl, composition of the invention+fenoxasulfone, composition of the invention+fentrazamide, composition of the invention+ferrous sulfate, composition of the invention+flamprop-M, composition of the invention+flazasulfuron, composition of the invention+florasulam, composition of the invention+fluazifop, composition of the invention+fluazifop-butyl, composition of the invention+fluazifop-P, composition of the invention+fluazifop-P-butyl, composition of the invention+fluazolate, composition of the invention+flucarbazone, composition of the invention+flucarbazone-sodium, composition of the invention+flucetosulfuron, composition of the invention+fluchloralin, composition of the invention+flufenacet, composition of the invention+flufenpyr, composition of the invention+flufenpyr-ethyl, composition of the invention+flumetralin, composition of the invention+flumetsulam, composition of the invention+flumiclorac, composition of the invention+flumiclorac-pentyl, composition of the invention+flumioxazin, composition of the invention+flumipropin, composition of the invention+fluometuron, composition of the invention+fluoroglycofen, composition of the invention+fluoroglycofen-ethyl, composition of the invention+fluoxaprop, composition of the invention+flupoxam, composition of the invention+flupropacil, composition of the invention+flupropanate, composition of the invention+flupyrsulfuron, composition of the invention+flupyrsulfuron-methyl-sodium, composition of the invention+flurenol, composition of the invention+fluridone, composition of the invention+fluorochloridone, composition of the invention+fluoroxypyr, composition of the invention+flurtamone, composition of the invention+fluthiacet, composition of the invention+fluthiacet-methyl, composition of the invention+fomesafen, composition of the invention+foramsulfuron, composition of the invention+fosamine, composition of the invention+glufosinate, composition of the invention+glufosinate-ammonium, composition of the invention+glyphosate, composition of the invention+halosulfuron, composition of the invention+halosulfuron-methyl, composition of the invention+haloxyfop, composition of the invention+haloxyfop-P, composition of the invention+HC-252, composition of the invention+hexazinone, composition of the invention+imazamethabenz, composition of the invention+imazamethabenz-methyl, composition of the invention+imazamox, composition of the invention+imazapic, composition of the invention+imazapyr, composition of the invention+imazaquin, composition of the invention+imazethapyr, composition of the invention+imazosulfuron, composition of the invention+indanofan, composition of the invention+indaziflam, composition of the invention+iodomethane, composition of the invention+iodosulfuron, composition of the invention+iodosulfuron-methyl-sodium, composition of the invention+ioxynil, composition of the invention+ipfencarbazone, composition of the invention+isoproturon, composition of the invention+ isouron, composition of the invention+isoxaben, composition of the invention+isoxachlortole, composition of the invention+isoxaflutole, composition of the invention+isoxapyrifop, composition of the invention+karbutilate, composition of the invention+lactofen, composition of the invention+lenacil, composition of the invention+linuron, composition of the invention+MAA, composition of the invention+MAMA, composition of the invention+MCPA, composition of the invention+MCPA-thioethyl, composition of the invention+MCPB, composition of the invention+mecoprop, composition of the invention+mecoprop-P, composition of the invention+mefenacet, composition of the invention+mefluidide, composition of the invention+mesosulfuron, composition of the invention+mesosulfuron-methyl, composition of the invention+mesotrione, composition of the invention+metam, composition of the invention+metamifop, composition of the invention+metamitron, composition of the invention+metazachlor, composition of the invention+metazosulfuron, composition of the invention+methabenzthiazuron, composition of the invention+methazole, composition of the invention+methylarsonic acid, composition of the invention+methyldymron, composition of the invention+methyl isothiocyanate, composition of the invention+metobenzuron, composition of the invention+metobromuron, composition of the invention+metolachlor, composition of the invention+S-metolachlor, composition of the invention+metosulam, composition of the invention+metoxuron, composition of the invention+metribuzin, composition of the invention+metsulfuron, composition of the invention+metsulfuron-methyl, composition of the invention+MK-616, composition of the invention+molinate, composition of the invention+monolinuron, composition of the invention+monosulfuron, composition of the invention+monosulfuron-ester, composition of the invention+MSMA, composition of the invention+naproanilide, composition of the invention+napropamide, composition of the invention+naptalam, composition of the invention+NDA-402989, composition of the invention+neburon, composition of the invention+nicosulfuron, composition of the invention+nipyraclofen, composition of the invention+n-methyl glyphosate, composition of the invention+nonanoic acid, composition of the invention+norflurazon, composition of the invention+oleic acid (fatty acids), composition of the invention+orbencarb, composition of the invention+orthosulfamuron, composition of the invention+oryzalin, composition of the invention+oxadiargyl, composition of the invention+oxadiazon, composition of the invention+oxasulfuron, composition of the invention+oxaziclomefone, composition of the invention+oxyfluorfen, composition of the invention+paraquat, composition of the invention+paraquat dichloride, composition of the invention+pebulate, composition of the invention+pendimethalin, composition of the invention+penoxsulam, composition of the invention+pentachlorophenol, composition of the invention+pentanochlor, composition of the invention+pentoxazone, composition of the invention+pethoxamid, composition of the invention+petrolium oils, composition of the invention+phenmedipham, composition of the invention+phenmedipham-ethyl, composition of the invention+picloram, composition of the invention+picolinafen, composition of the invention+pinoxaden, composition of the invention+piperophos, composition of the invention+potassium arsenite, composition of the invention+potassium azide, composition of the invention+pretilachlor, composition of the invention+primisulfuron, composition of the invention+primisulfuron-methyl, composition of the invention+prodiamine, composition of the invention+profluazol, composition of the invention+profoxydim, composition of the invention+prohexadione-calcium, composition of the invention+prometon, composition of the invention+prometryn, composition of the invention+propachlor, composition of the invention+propanil, composition of the invention+propaquizafop, composition of the invention+propazine, composition of the invention+propham, composition of the invention+propisochlor, composition of the invention+propoxycarbazone, composition of the invention+propoxycarbazone-sodium, composition of the invention+propyzamide, composition of the invention+prosulfocarb, composition of the invention+prosulfuron, composition of the invention+pyraclonil, composition of the invention+pyraflufen, composition of the invention+pyraflufen-ethyl, composition of the invention+pyrasulfotole, composition of the invention+pyrazolynate, composition of the invention+pyrazosulfuron, composition of the invention+pyrazosulfuron-ethyl, composition of the invention+pyrazoxyfen, composition of the invention+pyribenzoxim, composition of the invention+pyributicarb, composition of the invention+pyridafol, composition of the invention+pyridate, composition of the invention+pyriftalid, composition of the invention+pyriminobac, composition of the invention+pyriminobac-methyl, composition of the invention+pyrimisulfan, composition of the invention+pyrithiobac, composition of the invention+pyrithiobac-sodium, composition of the invention+pyroxasulfone, composition of the invention+pyroxulam, composition of the invention+quinclorac, composition of the invention+quinmerac, composition of the invention+quinoclamine, composition of the invention+quizalofop, composition of the invention+quizalofop-P, composition of the invention+quizalofop-ethyl, composition of the invention+quizalofop-P-ethyl, composition of the invention+rimsulfuron, composition of the invention+saflufenacil, composition of the invention+sethoxydim, composition of the invention+siduron, composition of the invention+simazine, composition of the invention+simetryn, composition of the invention+SMA, composition of the invention+sodium arsenite, composition of the invention+sodium azide, composition of the invention+sodium chlorate, composition of the invention+sulcotrione, composition of the invention+sulfentrazone, composition of the invention+sulfometuron, composition of the invention+sulfometuron-methyl, composition of the invention+sulfosate, composition of the invention+sulfosulfuron, composition of the invention+sulfuric acid, composition of the invention+tar oils, composition of the invention+2,3,6-TBA, composition of the invention+TCA, composition of the invention+TCA-sodium, composition of the invention+tebutam, composition of the invention+tebuthiuron, composition of the invention+tefuryltrione, composition of the invention+tembotrione, composition of the invention+tepraloxydim, composition of the invention+terbacil, composition of the invention+terbumeton, composition of the invention+terbuthylazine, composition of the invention+terbutryn, composition of the invention+thenylchlor, composition of the invention+thiazafluoron, composition of the invention+thiazopyr, composition of the invention+thifensulfuron, composition of the invention+thiencarbazone, composition of the invention+thifensulfuron-methyl, composition of the invention+thiobencarb, composition of the invention+tiocarbazil, composition of the invention+topramezone, composition of the invention+tralkoxydim, composition of the invention+triafamone, composition of the invention+tri-allate, composition of the invention+triasulfuron, composition of the invention+triaziflam, composition of the invention+tribenuron, composition of the invention+tribenuron-methyl, composition of the invention+tricamba, composition of the invention+triclopyr, composition of the invention+trietazine, composition of the invention+trifloxysulfuron, composition of the invention+trifloxysulfuron-sodium, composition of the invention+trifluralin, composition of the invention+triflusulfuron, composition of the invention+triflusulfuron-methyl, composition of the invention+trifop, composition of the invention+trifop-methyl, composition of the invention+trihydroxytriazine, composition of the invention+trinexapac-ethyl, composition of the invention+tritosulfuron, composition of the invention+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), composition of the invention+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5) and composition of the invention+4-hydroxy-3-[[2-(3-methoxypropyl)-6-(difluoromethyl)-3-pyridinyl]carbonyl]-bicyclo[3.2.1]oct-3-en-2-one.

Whilst compositions comprising a safener and a two-way mixture of a compound of formula (I) and another herbicide are explicitly disclosed above, the skilled man will appreciate that the invention extends to three-way, and further multiple combinations comprising the above two-way mixtures.

Particularly preferred mixture partners for use in the compositions of the invention are: 2,4-D, acetochlor, aminocyclopyrachlor, aminopyralid, atrazine, azimsulfuron, bensulfuron, bensulfuron-methyl, bentazon, benzobicyclon, bispyribac, bispyribac-sodium, bromobutide, bromoxynil, butachlor, butafenacil, cafenstrole, carfentrazone, cinosulfuron, clodinafop-propargyl, clomazone, clomeprop, clopyralid, cyclosulfamuron, cycloxydim, cyhalofop, cyhalofop-butyl, daimuron, dicamba, diclofop-methyl, diflufenzopyr-Na, dimethenamid, dimethenamid-P, diquat, diquat dibromide, esprocarb, ethoxysulfuron, fenoxaprop-ethyl, fenoxaprop-P-ethyl, fentrazamide, fenoxasulfone, florasulam, fluazifop-butyl, fluazifop-P-butyl, flufenacet, flumiclorac, flumioxazin, fluoroxypyr, flumetsulam, fluthiacet, fomesafen, foramsulfuron, glufosinate, glufosinate-ammonium, glyphosate, halosulfuron, halosulfuron-methyl, haloxyfop-methyl, haloxyfop-P-methyl, imazamethabenz-methyl, imazamox, imazosulfuron, indanofan, iodosulfuron-methyl-sodium, ipfencarbazone, isoxaflutole, MCPA, mecoprop, mecoprop-P, mefenacet, mesosulfuron-methyl, mesotrione, metamifop, metazosulfuron, metolachlor, s-metolachlor, metribuzin, metsulfuron, metsulfuron-methyl, MK-616, molinate, monosulfuron-ester, naptalam, nicosulfuron, orthosulfamuron, oxadiargyl, oxadiazon, oxaziclomefone, paraquat, paraquat dichloride, pendimethalin, penoxsulam, pentoxazone, pinoxaden, pretilachlor, primisulfuron-methyl, profoxydim, propanil, propaquizafop, prosulfuron, pyrachlonil, pyrazolynate, pyrazosulfuron, pyrazosulfuron-ethyl, pyroxsulam, pyrazoxyfen, pyribenzoxim, pyriftalid, pyriminobac-methyl, pyrimisulfan, pyroxasulfone, quinclorac, quizalofop-ethyl, quizalofop-P-ethyl, rimsulfuron, saflufencil, sethoxydim, simazine, tefuryltrione, tembotrione, terbuthylazine, thifensulfuron, topramezone, tralkoxydim, triafamone, triasulfuron, tribenuron-methyl, tritosulfuron and trifop-methyl.

In particular, when the composition of the invention is to be used on corn, the following mixing partners are preferred: 2,4-D, acetochlor, aminocyclopyrachlor, aminopyralid, atrazine, bentazon, bromoxynil, butafenacil, carfentrazone, clodinafop-propargyl, cycloxydim, dicamba, diflufenzopyr-Na, dimethenamid, dimethenamid-P, fenoxaprop-ethyl, fenoxaprop-P-ethyl, florasulam, fluazifop-butyl, fluazifop-P-butyl, flufenacet, flumiclorac, fluoroxypyr, flumetsulam, flumioxazin, fluthiacet, fomesafen, foramsulfuron, glufosinate, glyphosate, halosulfuron, halosulfuron-methyl, haloxyfop-methyl, haloxyfop-P-methyl, iodosulfuron-methyl-sodium, isoxaflutole, mesotrione, metolachlor, s-metolachlor, metribuzin, nicosulfuron, paraquat, pendimethalin, primisulfuron-methyl, propaquizafop, prosulfuron, pyroxasulfone, quizalofop-ethyl, quizalofop-P-ethyl, rimsulfuron, saflufencil, sethoxydim, simazine, tembotrione, terbuthylazine, topramezone and tritosulfuron.

In particular, when the composition of the invention is to be used on rice, the following mixing partners are preferred: 2,4-D, azimsulfuron, bensulfuron, bensulfuron-methyl, benzobicyclon, bispyribac, bispyribac-sodium, butachlor, cafenstrole, cinosulfuron, clomazone, clomeprop, clopyralid, cyclosulfamuron, cyhalofop, cyhalofop-butyl, daimuron, dicamba, diquat, diquat dibromide, esprocarb, ethoxysulfuron, fenoxaprop-P, fenoxaprop-P-ethyl, fentrazamide, florasulam, glufosinate-ammonium, halosulfuron, halosulfuron-methyl, imazamethabenz-methyl, imazamox, imazosulfuron, MCPA, mefenacet, metamifop, metsulfuron, metsulfuron-methyl, MK-616, molinate, glyphosate, orthosulfamuron, oxadiargyl, oxadiazon, paraquat dichloride, pendimethalin, penoxsulam, pretilachlor, profoxydim, propanil, pyrazolynate, pyrazosulfuron, pyrazosulfuron-ethyl, pyrazoxyfen, pyribenzoxim, pyriftalid, pyriminobac-methyl, pyrimisulfan, quinclorac, tefuryltrione, triasulfuron, trinexapac-ethyl, fenoxasulfone, ipfencarbazone, metazosulfuron, triafamone, mesotrione, indanofan, oxaziclomefone, bromobutide, pentoxazone and pyrachlonil.

In particular, when the composition of the invention is to be used on sugar cane, the following mixing partners are preferred: atrazine, ametryn, bicyclopyrone, 2,4-D, diuron, halosulfuron, mesotrione, pendimethalin and trifloxysulfuron.

For the avoidance of doubt, even if not explicitly stated above, the mixing partners may also be in the form of any suitable agrochemically acceptable ester or salt, as mentioned e.g. in The Pesticide Manual, Thirteenth Edition, British Crop Protection Council, 2003.

The mixing ratio of the compound of formula (I) to the mixing partner is preferably from 1:500 to 1000:1.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Example 1

Safening on Corn

Maize seeds were sown into standard soil in pots and cultivated under controlled conditions in a glasshouse (at 24/18° C. day/night; 16 hours light; 65% humidity).

When the plants were at the vegetative stage of 3 leaves they were sprayed with an aqueous spray solution containing a compound of formula (I) alone and in combination with a number of different herbicide safeners. All the compounds used for the spray solution were present as an EC or SC formulation respectively. In addition a non-ionic surfactant (X-77 Spreader) was added to form a 0.2% v/v solution.

The spray solution was applied with a cabinet tracksprayer with a flat fan nozzle (Teejet 11002VS) and an application volume of 200 L/ha (at 2 bar).

The test plants were then grown on in a glasshouse under controlled conditions (at 24/18° C. day/night; 16 hours light;

65% humidity) and watered twice a day. After 21 days the test was evaluated for general crop injury (100% equals total damage to plant; 0% equals no damage to plant).

Results are shown below in Table 1 as the mean % visual phytotoxicity of two replicates.

TABLE 1

Percentage damage caused to corn by compounds of formula (I) alone and in the presence of a number of safeners including N-(2-methoxybenzoyl)-4-[(methylaminocarbonyl)amino]benzenesulfonamide (Safener A).

| Composition | Rate (g a.i./ha) | |
|---|---|---|
| | 10 g/ha | 50 g/ha |
| Compound 1-21 Alone | 55.0 | 77.5 |
| 1-21 + 100 g/ha Benoxacor | 20.0 | 77.5 |
| 1-21 + 100 g/ha Cloquintocet-mexyl | 5.0 | 62.5 |
| 1-21 + 100 g/ha Isoxadifen-ethyl | 0.0 | 35.0 |
| 1-21 + 100 g/ha Cyprosulfamide | 0.0 | 15.0 |
| 1-21 + 100 g/ha Fluxofenim | 27.5 | 77.5 |
| 1-21 + 100 g/ha Mefenpyr-diethyl | 55.0 | 85.0 |
| 1-21 + 100 g/ha Dichlormid | 57.5 | 85.0 |
| 1-21 + 100 g/ha Safener A | 0.0 | 0.0 |

Example 2

Safening on Corn and Sweetcorn

Sweetcorn and Maize seeds were sown into standard soil in troughs and cultivated under controlled conditions in a glasshouse (at 24/18° C. day/night; 16 hours light, 65% humidity).

When the plants were at the vegetative stage of 2 leaves they were sprayed with an aqueous spray solution containing a compound of formula (I) alone and in combination with a number of different herbicide safeners. All the compounds used for the spray solution were present as technical material. In addition a non-ionic surfactant (X-77 Spreader) was added to a 0.2% v/v solution.

The spray solution was applied with a cabinet tracksprayer with a flat fan nozzle (Teeject 11002VS) and an application volume of 200 L/ha (at 2 bar).

The test plants were then grown on in a glasshouse under controlled conditions (at 24/18° C. day/night; 16 hours light; 65% humidity) and watered twice a day. After 21 days the test was evaluated for general crop injury (100% equals total damage to plant; 0% equals no damage to plant).

Results are shown below in Tables 2 and 3 as the mean % visual phytotoxicity of three replicates.

TABLE 2

Percentage damage caused to corn (variety Claxxon) by compounds of formula (I) alone and in the presence of a number of safeners including N-(2-methoxybenzoyl)-4-[(methylaminocarbonyl)amino]benzene-sulfonamide (Safener A).

| Composition | Rate (g a.i./ha) | |
|---|---|---|
| | 10 g/ha | 50 g/ha |
| Compound 1-5 Alone | 27 | 65 |
| 1-5 + 10 g/ha Benoxacor | 8 | |
| 1-5 + 10 g/ha Cloquintocet-mexyl | 17 | |
| 1-5 + 10 g/ha Isoxadifen-ethyl | 0 | |
| 1-5 + 10 g/ha Cyprosulfamide | 0 | |
| 1-5 + 10 g/ha Concep III* | 5 | |
| 1-5 + 10 g/ha Mefenpyr-diethyl | 23 | |
| 1-5 + 10 g/ha Dichlormid | 7 | |
| 1-5 + 10 g/ha Safener A | 0 | |
| 1-5 + 50 g/ha Benoxacor | | 43 |
| 1-5 + 50 g/ha Cloquintocet-mexyl | | 48 |
| 1-5 + 50 g/ha Isoxadifen-ethyl | | 32 |
| 1-5 + 50 g/ha Cyprosulfamide | | 13 |
| 1-5 + 50 g/ha Concep III* | | 43 |
| 1-5 + 50 g/ha Mefenpyr-diethyl | | 63 |
| 1-5 + 50 g/ha Dichlormid | | 60 |
| 1-5 + 50 g/ha Safener A | | 0 |
| Compound 1-21 Alone | 10 | 73 |
| 1-21 + 10 g/ha Benoxacor | 20 | |
| 1-21 + 10 g/ha Cloquintocet-mexyl | 45 | |
| 1-21 + 10 g/ha Isoxadifen-ethyl | 23 | |
| 1-21 + 10 g/ha Cyprosulfamide | 0 | |
| 1-21 + 10 g/ha Concep III* | 12 | |
| 1-21 + 10 g/ha Mefenpyr-diethyl | 17 | |
| 1-21 + 10 g/ha Dichlormid | 15 | |
| 1-21 + 10 g/ha Safener A | 0 | |
| 1-21 + 50 g/ha Benoxacor | | 68 |
| 1-21 + 50 g/ha Cloquintocet-mexyl | | 77 |
| 1-21 + 50 g/ha Isoxadifen-ethyl | | 75 |
| 1-21 + 50 g/ha Cyprosulfamide | | 40 |
| 1-21 + 50 g/ha Concep III* | | 60 |
| 1-21 + 50 g/ha Mefenpyr-diethyl | | 73 |
| 1-21 + 50 g/ha Dichlormid | | 65 |
| 1-21 + 50 g/ha Safener A | | 20 |

*Concep III contains 74.3% fluxofenim.

TABLE 3

Percentage damage caused to sweetcorn (variety Sundance) by compounds of formula (I) alone and in the presence of a number of safeners including N-(2-methoxybenzoyl)-4-[(methylaminocarbonyl)amino]benzenesulfonamide (Safener A).

| Composition | Rate (g a.i./ha) | |
|---|---|---|
| | 50 g/ha | 100 g/ha |
| Compound 1-5 Alone | 47 | 80 |
| 1-5 + 50 g/ha Benoxacor | 33 | |
| 1-5 + 50 g/ha Cloquintocet-mexyl | 23 | |
| 1-5 + 50 g/ha Isoxadifen-ethyl | 33 | |
| 1-5 + 50 g/ha Cyprosulfamide | 0 | |
| 1-5 + 50 g/ha Concep III* | 27 | |
| 1-5 + 50 g/ha Mefenpyr-diethyl | 58 | |
| 1-5 + 50 g/ha Dichlormid | 43 | |
| 1-5 + 50 g/ha Safener A | 0 | |
| 1-5 + 100 g/ha Benoxacor | | 62 |
| 1-5 + 100 g/ha Cloquintocet-mexyl | | 30 |
| 1-5 + 100 g/ha Isoxadifen-ethyl | | 70 |
| 1-5 + 100 g/ha Cyprosulfamide | | 7 |
| 1-5 + 100 g/ha Concep III* | | 72 |
| 1-5 + 100 g/ha Mefenpyr-diethyl | | 95 |
| 1-5 + 100 g/ha Dichlormid | | 83 |
| 1-5 + 100 g/ha Safener A | | 0 |
| Compound 1-21 Alone | 88 | 98 |
| 1-21 + 50 g/ha Benoxacor | 68 | |
| 1-21 + 50 g/ha Cloquintocet-mexyl | 78 | |
| 1-21 + 50 g/ha Isoxadifen-ethyl | 72 | |
| 1-21 + 50 g/ha Cyprosulfamide | 0 | |
| 1-21 + 50 g/ha Concep III* | 62 | |
| 1-21 + 50 g/ha Mefenpyr-diethyl | 33 | |
| 1-21 + 50 g/ha Dichlormid | 70 | |
| 1-21 + 50 g/ha Safener A | 0 | |
| 1-21 + 100 g/ha Benoxacor | | 93 |
| 1-21 + 100 g/ha Cloquintocet-mexyl | | 92 |
| 1-21 + 100 g/ha Isoxadifen-ethyl | | 95 |
| 1-21 + 100 g/ha Cyprosulfamide | | 15 |
| 1-21 + 100 g/ha Concep III* | | 82 |

TABLE 3-continued

Percentage damage caused to sweetcorn (variety Sundance) by compounds of formula (I) alone and in the presence of a number of safeners including N-(2-methoxybenzoyl)-4-[(methylaminocarbonyl)amino]benzenesulfonamide (Safener A).

| Composition | Rate (g a.i./ha) | |
|---|---|---|
| | 50 g/ha | 100 g/ha |
| 1-21 + 100 g/ha Mefenpyr-diethyl | | 92 |
| 1-21 + 100 g/ha Dichlormid | | 78 |
| 1-21 + 100 g/ha Safener A | | 2 |

*Concep III contains 74.3% fluxofenim.

Example 3

Safening on Sugarcane (Variety SP803280)

Sugarcane stem sections were sown into standard soil in troughs and cultivated under controlled conditions in a glasshouse (at 30/20° C. day/night; 18 hours light, 75% humidity).

When the plants were at the vegetative stage of 3-4 leaves they were sprayed with an aqueous spray solution containing a compound of formula (I) alone and in combination with a number of different herbicide safeners. All the compounds used for the spray solution were present as technical material. In addition a non-ionic surfactant (X-77 Spreader) was added to a 0.2% v/v solution.

The spray solution was applied with a cabinet tracksprayer with a flat fan nozzle (Teeject 11002VS) and an application volume of 200 L/ha (at 2 bar).

The test plants were then grown on in a glasshouse under controlled conditions (at 30/20° C. day/night; 18 hours light; 75% humidity) and watered twice a day. After 26 days the test was evaluated for general crop injury (100% equals total damage to plant; 0% equals no damage to plant).

Results are shown below in Table 4 as the mean % visual phytotoxicity of four replicates.

TABLE 4

Percentage damage caused to sugarcane (variety SP803280) by compounds of formula (I) alone and in the presence of a number of safeners including N-(2-methoxybenzoyl)-4-[(methylaminocarbonyl)amino]benzenesulfonamide (Safener A).

| Composition | Rate (g a.i./ha) | |
|---|---|---|
| | 62.5 g/ha | 250 g/ha |
| Compound 1-5 Alone | 3 | 34 |
| 1-5 + 100 g/ha Benoxacor | 3 | 76 |
| 1-5 + 100 g/ha Cloquintocet-mexyl | 18 | 41 |
| 1-5 + 100 g/ha Isoxadifen-ethyl | 0 | 18 |
| 1-5 + 100 g/ha Cyprosulfamide | 5 | 35 |
| 1-5 + 100 g/ha Concep III* | 0 | 10 |
| 1-5 + 100 g/ha Mefenpyr-diethyl | 15 | 38 |
| 1-5 + 100 g/ha Dichlormid | 13 | 94 |
| 1-5 + 100 g/ha Safener A | 0 | 3 |
| Compound 1-21 Alone | 44 | 58 |
| 1-21 + 100 g/ha Benoxacor | 48 | 63 |
| 1-21 + 100 g/ha Cloquintocet-mexyl | 46 | 75 |
| 1-21 + 100 g/ha Isoxadifen-ethyl | 0 | 51 |
| 1-21 + 100 g/ha Cyprosulfamide | 31 | 88 |
| 1-21 + 100 g/ha Concep III* | 3 | 38 |
| 1-21 + 100 g/ha Mefenpyr-diethyl | 20 | 71 |
| 1-21 + 100 g/ha Dichlormid | 34 | 74 |
| 1-21 + 100 g/ha Safener A | 0 | 0 |

*Concep III contains 74.3% fluxofenim.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A composition for protecting crop plants from injury of a pyridine derivative herbicide of formula (I)

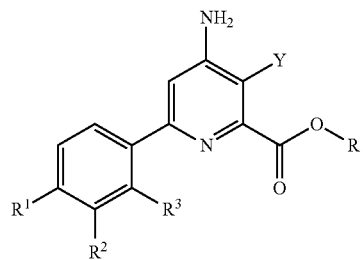

or a salt or N-oxide thereof wherein Y is chloro or bromo, R is hydrogen, $C_{1-8}$ alkyl, $C_{2-5}$ alkenyl, $C_{3-5}$ alkynyl, aryl $C_{1-2}$ alkyl, $C_{1-4}$ alkoxy $C_{1-4}$ alkyl or $C_{1-4}$ alkoxy $C_{1-4}$ alkoxy $C_{1-2}$ alkyl, $R^1$ is chloro or bromo, $R^2$ is $C_{1-2}$ alkoxy and $R^3$ is chloro or fluoro and wherein said composition comprises, in addition to the pyridine derivative herbicide of formula (I), the safener N-(2-methoxybenzoyl)-4-[(methylaminocarbonyl)amino] benzenesulfonamide, wherein the safener reduces the injury to the crop plants caused by the pyridine derivative herbicide of formula (I).

2. The composition according to claim 1, wherein Y is chloro.

3. The composition according to claim 1, wherein $R^1$ is chloro.

4. The composition according to claim 1, wherein $R^2$ is methoxy.

5. The composition according to claim 1, wherein $R^3$ is fluoro.

6. The composition according to claim 1, wherein R is hydrogen, $C_{1-4}$ alkyl, $C_{3-4}$ alkenyl, arylmethyl or $C_{1-4}$ alkoxy $C_{1-2}$ alkyl.

7. The composition according to claim 6, wherein R is hydrogen or methyl.

8. The composition according to claim 7, wherein R is hydrogen.

9. The composition according to claim 8, wherein the compound of formula (I) is present as an alkali metal, an alkaline earth metal, ammonia or amine salt.

10. A method for protecting crops of useful plants from the injury of a herbicide of formula (I) as defined in claim 1, which comprises applying to the locus of the useful plants the safener N-(2-methoxybenzoyl)-4-[(methylaminocarbonyl) amino]benzenesulfonamide.

11. The method of claim 10, wherein the useful plant is selected from the group consisting of maize, rice and sugar cane.

12. A method for combating weeds in crops of useful plants, which comprises treating the useful plants, seeds or cuttings thereof or the locus of the useful plants simultaneously or at separate times with the pyridine derivative herbicide of formula (I) as defined in claim 1 and the safener N-(2-methoxybenzoyl)-4-[(methylaminocarbonyl)amino]benzenesulfonamide, wherein the safener reduces the injury to the crop plants caused by the pyridine derivative herbicide of formula (I).

13. The method of claim 12, wherein the useful plant is selected from the group consisting of maize, rice and sugar cane.

* * * * *